United States Patent
Bienkowski et al.

(10) Patent No.: US 9,989,486 B2
(45) Date of Patent: Jun. 5, 2018

(54) INDUCTION THERMOGRAPHY METHOD

(71) Applicant: Siemens Aktiengesellschaft, Munich (DE)

(72) Inventors: Lukasz Adam Bienkowski, Munich (DE); Matthias Goldammer, Munich (DE); Christian Homma, Kirchheim b. Munich (DE); Max Rothenfusser, Munich (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 173 days.

(21) Appl. No.: 15/024,039

(22) PCT Filed: Sep. 11, 2014

(86) PCT No.: PCT/EP2014/069345
§ 371 (c)(1),
(2) Date: Mar. 23, 2016

(87) PCT Pub. No.: WO2015/043963
PCT Pub. Date: Apr. 2, 2015

(65) Prior Publication Data
US 2016/0231261 A1    Aug. 11, 2016

(30) Foreign Application Priority Data
Sep. 25, 2013  (DE) .......... 10 2013 219 311

(51) Int. Cl.
*G01N 25/72* (2006.01)
*G01J 5/02* (2006.01)
*G01J 5/00* (2006.01)

(52) U.S. Cl.
CPC ........... *G01N 25/72* (2013.01); *G01J 5/02* (2013.01); *G01J 2005/0085* (2013.01)

(58) Field of Classification Search
CPC ..... G01J 2005/0085; G01J 5/02; G01N 25/72
(Continued)

(56) References Cited

U.S. PATENT DOCUMENTS

| 9,261,473 B2 | 2/2016 | Yahaba et al. ......... G01N 25/72 |
| 2007/0217672 A1* | 9/2007 | Shannon ............... G06T 7/0006 382/152 |

(Continued)

FOREIGN PATENT DOCUMENTS

| DE | 102009031605 A1 | 1/2011 |
| DE | 102011018263 A1 | 10/2012 |

(Continued)

OTHER PUBLICATIONS

Gao et al, Ferrite-yoke based pulsed induction thermography for cracks quantitative evaluation (Year: 2015).*

(Continued)

*Primary Examiner* — Shan E Elahi
(74) *Attorney, Agent, or Firm* — Slayden Grubert Beard PLLC

(57) ABSTRACT

A method for induction thermography includes acquiring a plurality of images or an object at each of a plurality of imaging directions, and deriving a combined Fourier-transformed image from the images taken at different imaging directions to detect defects in the object.

19 Claims, 1 Drawing Sheet

(58) Field of Classification Search
USPC .......................................................... 348/165
See application file for complete search history.

(56) References Cited

U.S. PATENT DOCUMENTS

| | | | | |
|---|---|---|---|---|
| 2007/0290134 | A1* | 12/2007 | Key | G01N 25/72 250/340 |
| 2008/0137105 | A1* | 6/2008 | Howard | G01N 25/72 356/630 |
| 2010/0292938 | A1* | 11/2010 | Vrana | G01N 25/72 702/35 |
| 2011/0159831 | A1* | 6/2011 | Jiang | H04L 25/0204 455/226.3 |
| 2013/0121615 | A1* | 5/2013 | Intwala | G06T 5/10 382/280 |
| 2013/0242309 | A1* | 9/2013 | Yuan | G01B 9/02004 356/479 |
| 2014/0249689 | A1* | 9/2014 | Bienkowski | G06F 3/017 700/299 |

FOREIGN PATENT DOCUMENTS

| | | |
|---|---|---|
| DE | 102012015167 A1 | 3/2013 |
| DE | 102012222933 A1 | 6/2013 |
| WO | 2015/043963 A1 | 4/2015 |

OTHER PUBLICATIONS

Moderhak, M., "Fourier Based Stabilisation of Thermal Images in Dynamic Thermography," 10$^{th}$ International Conference on Quantitative InfraRed Thermography, URL: http://www.ndt.net/article/qirt2010/papers/qirt2010-093.pdf, 9 pages, Jul. 27, 2010.

Montanani, R. et al., "Ultrasound Lock-In Thermography as a Quantitative Technique for Quality Control Assessment of Case Iron Turbocharger Components," 10$^{th}$ International Conference on Quantitative InfraRed Thermography, URL: http://qirt.gel.ulaval.ca/archives/qirt2010/papers/QIRT2010-097.pdf, 8 pages, Jul. 27, 2010.

German Office Action, Application No. 102013219311.4, 5 pages, dated Jan. 31, 2014.

International Search Report and Written Opinion, Application No. PCT/EP2014/069345, 16 pages, dated Nov. 7, 2014.

* cited by examiner

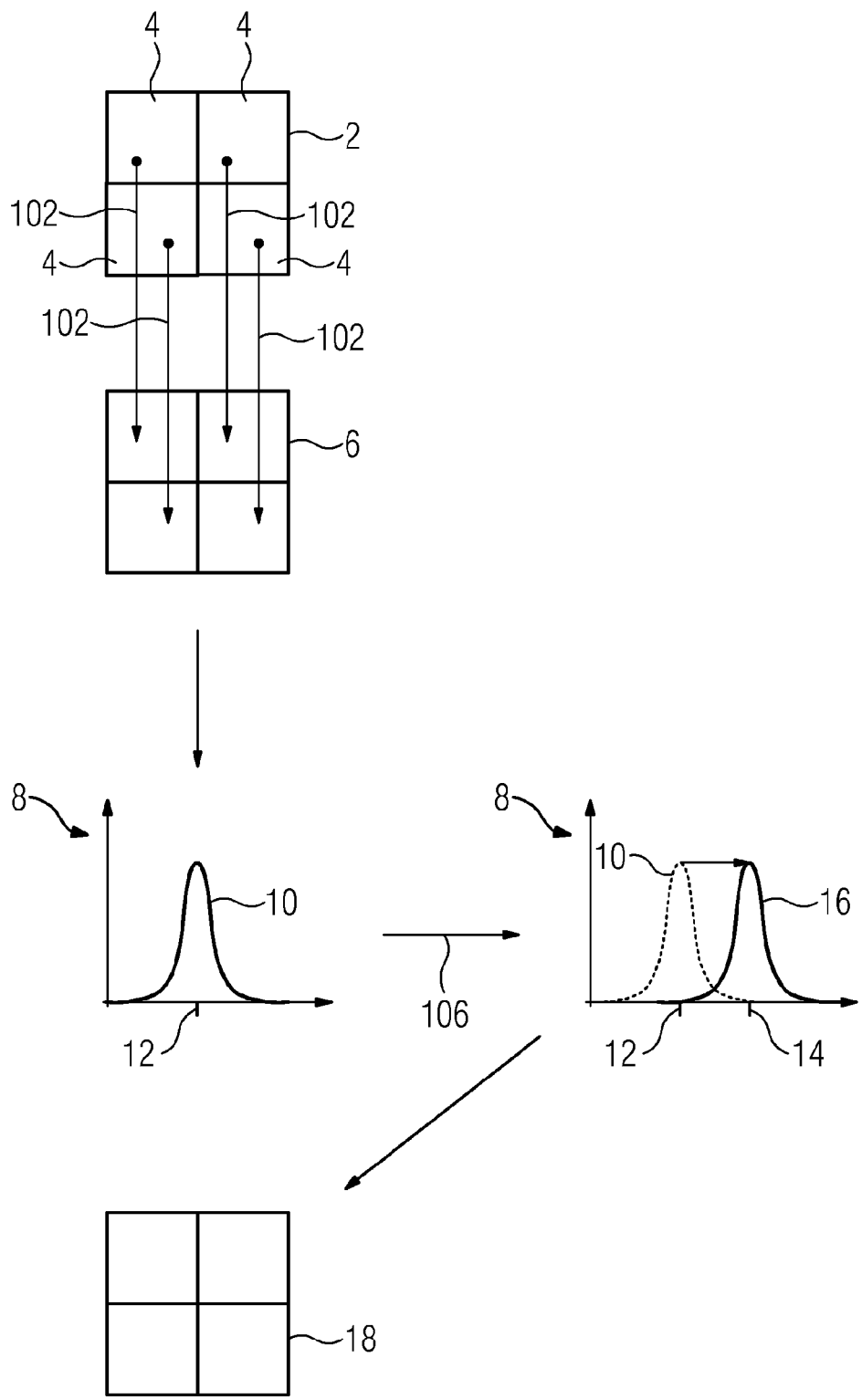

INDUCTION THERMOGRAPHY METHOD

CROSS-REFERENCE TO RELATED APPLICATIONS

This application is a U.S. National Stage Application of International Application No. PCT/EP2014/069345 filed Sep. 11, 2014, which designates the United States of America, and claims priority to DE Application No. 10 2013 219 311.4 filed Sep. 25, 2013, the contents of which are hereby incorporated by reference in their entirety.

TECHNICAL FIELD

The invention relates to an induction thermography method.

BACKGROUND

For the inspection of workpieces or components, induction thermography may be used as an inspection method. In this case, a temperature profile, for example on a surface of the object to be inspected, is acquired with an infrared camera in a multiplicity of images. In general, distinction is made between active thermography (with stimulation) and passive thermography (without stimulation). In this case, induction thermography constitutes an active method.

In induction thermography, an induction current is generated by means of a coil, or an inductor, in the object to be inspected. This leads to heating of the object by ohmic losses, so that a thermal profile can be detected by means of the infrared camera from a resulting heat distribution on the surface of the object.

If the object to be inspected has defects, in particular cracks, then the induced current must flow around these or through individual contact positions of the crack edges. For this reason, a local current density and therefore heating due to ohmic losses is increased at the defects, for example at the cracks. This increased heating of the defects is visible in the infrared image.

For inspection of the object, it is necessary to bring the coil particularly close to the object, since the induced current flows preferentially in the vicinity of the coil. For this reason, however, only local inspection in a particular region of the object can take place. If the entire object or a wide-ranging region of the object is intended to be studied, the measurement must be repeated several times, that is to say from different acquisition directions with corresponding displacement of the coil. According to the prior art, for each individual measurement the multiplicity of images are subjected to a mathematical analysis, which delivers a result image for each measurement. Typically, depending on the size of the object to be inspected, about 80 images (result images) are generated, which need to be observed and analyzed individually by a tester. Because of such individual observation by the tester, the defect detectability is impaired, since typically only a small section of the thermographic image respectively contains essential information while as a result of the analysis the rest of the image has a high level of noise or shows no signal, and therefore no information. Furthermore, individual defects may readily be visible in images of a plurality of measurements, which can lead to inefficient multiple observation of the same defect.

SUMMARY

One embodiment provides an active induction thermography method, wherein a multiplicity of images of an object to be inspected are respectively acquired by means of a camera for a multiplicity of acquisition directions, wherein the following steps are carried out for each individual acquisition direction: derivation of a complex-value Fourier-transformed image from the images; determination of an average phase value from the Fourier-transformed image; wherein a phase-corrected Fourier-transformed image is derived from the average phase value and the Fourier-transformed image for each acquisition direction, so that the phase-corrected Fourier-transformed images then have an essentially equal average phase value; and wherein a combined Fourier-transformed image is derived from the phase-corrected Fourier-transformed images.

In a further embodiment, for each acquisition direction, a frequency distribution of the phase values present in the Fourier-transformed image is used for the derivation of the respective average phase value.

In a further embodiment, a most frequent phase value is respectively derived from the frequency distributions.

In a further embodiment, a centroid of the frequency distributions is respectively determined.

In a further embodiment, the frequency distributions are filtered using a Savitzky-Golay filter.

In a further embodiment, the numerical sum of the phase-corrected Fourier-transformed images is used for the derivation of the combined Fourier-transformed image.

In a further embodiment, at least 10 images are acquired at least for one acquisition direction.

In a further embodiment, the images of at least one acquisition direction are acquired in less than one second.

In a further embodiment, a combined phase and/or amplitude image is derived from the combined Fourier-transformed image.

In a further embodiment, at least the combined phase image is displayed in real time on a play screen.

BRIEF DESCRIPTION OF THE DRAWINGS

Aspects of the invention are discussed below with reference to the single FIGURE, FIG. 1, which shows a schematic sequence of the method for one acquisition direction, according to one embodiment.

DETAILED DESCRIPTION

Embodiments of the present invention provide a method which allows improved defect detection of objects to be inspected.

In the disclosed active induction thermography method, a multiplicity of images of an object to be inspected are respectively acquired by means of a camera for a multiplicity of acquisition directions. In this case, the following steps are carried out for each individual acquisition direction, i.e. for each individual measurement:

derivation of a complex-value Fourier-transformed image from the individual images;

determination of an average phase value from the Fourier-transformed image.

A phase-corrected Fourier-transformed image is derived from the average phase value which has been determined and the Fourier-transformed image for each acquisition direction, so that the phase-corrected Fourier-transformed images then have an essentially equal average phase value. The phase-corrected Fourier-transformed images of the individual acquisition directions are then collated to form a combined Fourier-transformed image.

According to the disclosed method, a suitable image on which the inspection of the object is intended to be based is advantageously derived from the multiplicity of images. For this reason, a tester merely has to observe this derived phase-corrected, Fourier-transformed combined image. This significantly facilitates the error correction.

In other words, the method may be described as follows:

A multiplicity of images of the object to be inspected are respectively obtained for an acquisition direction of the camera. A Fourier-transformed image is derived from these images for each acquisition direction.

In order to carry out the Fourier transform, the images are considered as a matrix $A_{mn}(i,j)$ with real-value entries, for example. In this case, m corresponds to the $m^{th}$ acquisition direction, or measurement, n corresponds to the $n^{th}$ image from the $m^{th}$ acquisition direction, and the indices i,j denote the pixels of the two-dimensional image. The Fourier-transformed image $F_m(i,j)$ is then, for example, derived by the functional relationship $$F_m(i, j) = \sum_{n=1}^{N} A_{mn}(i, j) e^{2\pi i \frac{(n-1)}{N}},$$

where N denotes the total number of images in the respective acquisition direction.

It is therefore sufficient to observe only one frequency of the Fourier transform. According to the aforementioned functional relationship, the fundamental frequency is used here. In general, however, other frequencies can also be taken into consideration.

As a result of the complex-value Fourier transform, the Fourier-transformed images $F_m(i,j)$ of the acquisition directions have one amplitude and phase value per pixel (i,j). From the multiplicity of these phase values of a Fourier-transformed image for an acquisition direction, an average phase value $\varphi_m$ is determined. The average phase value is in this case to be understood as a value which is representative of the multiplicity of phase values. In order to determine the average phase value, many methods may generally be used. The choice of the method may depend here on the individual case.

In a further step, the Fourier-transformed images of each acquisition direction are phase-corrected by means of the respective average phase value. This is intended to mean that, for each acquisition direction, the phase values of all the pixels of the Fourier-transformed image are transformed in such a way that an average phase value re-derived from the phase-corrected Fourier-transformed images for each acquisition direction has essentially the same numerical value.

For example, the difference $\Delta\varphi_m$ of the average phase value from the phase value $\pi/2$ may be determined for each acquisition direction. If all the phase values of the Fourier-transformed images of all the acquisition directions m are then phase-corrected according to the relation $F_{m,corrected}(i,j)=F_m(i,j)e^{i\Delta\varphi_m}$, then the phase-corrected Fourier-transformed images $F_{m,corrected}(i,j)$ respectively have an average phase value of $\pi/2$. In this way, the phases of the Fourier-transformed images of the acquisition directions are matched to one another. Then, in a further step of the method, a combined phase-corrected Fourier-transformed image of the object to be inspected is derived from the individual phase-corrected images of the individual acquisition directions. For example, a numerical sum $F(i,j)=\Sigma_{m=1}^{M}F_{m,corrected}(i,j)$ of the phase-corrected images of the acquisition directions may be formed. Here, M denotes the total number of acquisition directions. Advantageously, the phases of the individual images contributing to the sum have been corrected and matched to one another before the formation of the sum, i.e. before the formation of the combined Fourier-transformed image F(i,j). In this way, errors which are created during collation of the individual images to form a combined image may be significantly reduced. The coherent, i.e. in-phase, superposition of the individual images to form a combined image of the object to be inspected furthermore increases the signal-to-noise ratio of the inspection. In general, the combined Fourier-transformed image F(i,j) has both amplitude and phase values from which a combined amplitude and phase image can be derived. It is found that, in particular, the combined phase image is advantageous for the evaluation of an object to be inspected.

Furthermore, the method may provide the advantage that a tester only has to observe a single image, namely the combined Fourier-transformed and phase-corrected image F(i,j) of the object to be inspected, for the assessment of defects. With the disclosed method, the usual 20 to 80 images according to the prior art may therefore be advantageously merged or combined into a single image. If the inductor for heating the object to be inspected is furthermore rotated and/or twisted during the various measurements from the different acquisition directions, then the advantage is obtained of better detectability of defects, particularly of linear cracks, which react sensitively to different current directions.

According to one embodiment, for each acquisition direction, a frequency distribution of the phase values present in the Fourier-transformed images is used for the derivation of the respective average phase value. For each acquisition direction, a multiplicity of images are acquired. By the Fourier transform, which combines this multiplicity of images to form a Fourier-transformed image with complex values, an amplitude value and a phase value is derived for each pixel of the combined Fourier-transformed image. In other words, each pixel of the image has in particular a phase value. If a frequency distribution of the phase values of a Fourier-transformed image is determined, then the average phase value can be determined therefrom. The average phase value is then representative of the phase values occurring in the Fourier-transformed image.

According to another embodiment, a most frequent phase value is derived from the frequency distribution. In this way, the average phase value corresponds to the phase value which, according to the frequency distribution, occurs most often in the Fourier-transformed image. The average phase value is then used for the phase correction of the Fourier-transformed image. For example, for each measurement from each acquisition direction, the phase difference between this most frequent phase value and a fixed phase value, in particular $\pi/2$, is determined.

In one embodiment, a centroid of the frequency distribution is determined. In this way, the average phase value can advantageously be established as a centroid, i.e. as a phase centroid of the frequency distribution. As a result of the determination of the centroid, the shape of the frequency distribution is also advantageously involved, so that the detection of defects is thereby increased.

According to one embodiment, the frequency distributions are filtered using a Savitzky-Golay filter. In this way, noise in the frequency distributions, or in the histogram, is advantageously suppressed. This facilitates the derivation of the most frequent phase value and/or of the phase centroid of the histogram, or of another quantity from the frequency distribution. For example, the derivation of higher moments of the frequency distribution may also be advantageous.

According to another embodiment, the numerical sum of the phase-corrected Fourier-transformed images is used for the derivation of the combined Fourier-transformed image. In this way, the combined Fourier-transformed image is the average value of the phase-corrected Fourier-transformed images. A further numerical factor, which scales the sum, may be provided.

In one embodiment, at least 10 images are acquired from each acquisition direction. Owing to the acquisition of a multiplicity of images from each acquisition direction, detection of defects is significantly increased. Furthermore, acquisition of a multiplicity of images is advantageous since propagation of the heat in and/or on a surface of the object to be inspected can be recorded. The at least 10 images consequently form a video, or a film, of the heat propagation. In another advantageous refinement, the images of at least one acquisition direction are acquired in less than one second. In this way, the profile of the heat, or of the heat propagation, as a function of time is advantageously recorded in real time.

According to one embodiment, a combined phase and/or amplitude image is derived from the combined complex-value Fourier-transformed image. In general, any complex number can be decomposed into an amplitude value (amplitude) and a phase value (phase). A combined Fourier-transformed image is represented by complex-value pixels, so that an amplitude and/or phase value can be derived for each pixel. This derived total set of the individual amplitude and/or phase values then forms the combined amplitude and/or phase image. The combined phase image is particularly advantageous since defects can be detected particularly well in the combined phase image.

According to one embodiment, at least the combined phase image is displayed in real time on a play screen. In this way, the tester can follow the inspection of the object to be inspected in real time. For example, the time difference which is due to latency times is less than one second. This may be achieved by software optimizations, for example multithreading.

FIG. 1, the sole FIGURE, shows a schematic sequence of the method for one acquisition direction, according to one embodiment. A thermographic image 2 of an object to be inspected is obtained from an arbitrary acquisition direction. In this exemplary embodiment, the image 2 comprises merely four pixels 4. From a multiplicity of images 2, a combined Fourier-transformed image 6 is derived by a Fourier transform 102. Each of the four pixels 4 therefore has an amplitude value and a phase value in the Fourier-transformed image 6. The phase values, of which there are four in this exemplary embodiment, are plotted in a histogram 8 and a frequency distribution 10 is therefore compiled. A most frequent phase value 12 (average phase value 12) is derived from the frequency distribution 10.

By means of the most frequent phase value 12, the individual phase values of the pixels are phase-corrected 106 in such a way as to produce a frequency distribution 16 which is shifted relative to the frequency distribution 10. In this case, the most frequent phase value 14 now has the value $\pi/2$. The individual phase-corrected pixels 4 now form a phase-corrected Fourier-transformed image 18. In this way, the phase-corrected average phase value 14 of each acquisition direction is now $\pi/2$.

The phase-corrected Fourier-transformed images 18 of the individual acquisition directions are collated to form a combined phase-corrected Fourier-transformed image by summation. Since the phase values have been corrected, that is to say they have been set to the same phase value, before the formation of the sum of the phase-corrected Fourier-transformed images, the formation of the sum is coherent and errors, for example due to displacement and/or rotation of the camera, are thus reduced. In particular, errors which result from residual heat of the preceding measurements are computationally corrected. Defects are therefore detected significantly better.

What is claimed is:

1. A method for active induction thermography, comprising:
   inducing a current in an object to be inspected;
   using a camera to acquire a plurality of infrared images of the object at each of a plurality of acquisition directions,
   for each of the plurality of acquisition directions:
      deriving a complex-value Fourier-transformed image from the plurality of images acquired at that acquisition direction;
      determining an average phase value from the Fourier-transformed image; and
      deriving a phase-corrected Fourier-transformed image from the average phase value and the Fourier-transformed image,
   wherein the phase-corrected Fourier-transformed images for the plurality of acquisition directions have an essentially equal average phase value with respect to each other, and
   deriving a combined Fourier-transformed image from the phase-corrected Fourier-transformed images for the plurality of acquisition directions, and
   identifying defects in the object based on increased heating due to ohmic losses visible in the combined Fourier-transformed image.

2. The method of claim 1, comprising, for each acquisition direction, using a frequency distribution of phase values present in the Fourier-transformed image for the derivation of the respective average phase value.

3. The method of claim 2, comprising deriving a most frequent phase value from the frequency distributions.

4. The method of claim 2, comprising determining a centroid of the frequency distributions.

5. The method of claim 2, comprising filtering the frequency distributions using a Savitzky-Golay filter.

6. The method of claim 1, comprising deriving the combined Fourier-transformed image based on a numerical sum of the phase-corrected Fourier-transformed images.

7. The method of claim 1, comprising acquiring at least 10 images at least for one of the acquisition directions.

8. The method of claim 1, comprising acquiring the images for at least one of the acquisition directions in less than one second.

9. The method of claim 1, comprising deriving at least one of a combined phase image or a combined amplitude image from the combined Fourier-transformed image.

10. The method of claim 1, comprising:
    deriving a combined phase image from the combined Fourier-transformed image, and
    displaying the combined phase image in real time on a display device.-

11. A method for active induction thermography, comprising:
inducing a current in an object to be inspected;
acquiring a plurality of infrared images of the object at each of a plurality of acquisition directions,
for each of the plurality of acquisition directions:
deriving a complex-value Fourier-transformed image from the plurality of images acquired at that acquisition direction;
determining an average phase value from the Fourier-transformed image; and
deriving a phase-corrected Fourier-transformed image from the average phase value and the Fourier-transformed image,
wherein the phase-corrected Fourier-transformed images for the plurality of acquisition directions have an essentially equal average phase value with respect to each other,
deriving a combined Fourier-transformed image from the phase-corrected Fourier-transformed images for the plurality of acquisition directions, and
identifying defects in the object based on increased heating due to ohmic losses visible in the combined Fourier-transformed image.

12. The method of claim 11, comprising, for each acquisition direction, using a frequency distribution of phase values present in the Fourier-transformed image for the derivation of the respective average phase value.

13. The method of claim 12, comprising deriving a most frequent phase value from the frequency distributions.

14. The method of claim 12, comprising determining a centroid of the frequency distributions.

15. The method of claim 12, comprising filtering the frequency distributions using a Savitzky-Golay filter.

16. The method of claim 11, comprising deriving the combined Fourier-transformed image based on a numerical sum of the phase-corrected Fourier-transformed images.

17. The method of claim 11, comprising acquiring at least 10 images at least for one of the acquisition directions.

18. The method of claim 11, comprising deriving at least one of a combined phase image or a combined amplitude image from the combined Fourier-transformed image.

19. The method of claim 11, comprising:
deriving a combined phase image from the combined Fourier-transformed image, and
displaying the combined phase image in real time on a display device.

* * * * *